United States Patent [19] [11] 4,061,722
Bodor [45] Dec. 6, 1977

[54] SELECTED QUATERNARY AMMONIUM SALTS OF PILOCARPINE USEFUL IN REDUCING INTRAOCULAR PRESSURE IN WARM-BLOODED ANIMALS

[75] Inventor: Nicolae S. Bodor, Lawrence, Kans.
[73] Assignee: INTERx Research Corporation, Lawrence, Kans.
[21] Appl. No.: 680,437
[22] Filed: Apr. 26, 1976
[51] Int. Cl.² .................. A61K 31/415; C07D 233/64
[52] U.S. Cl. ................................. 424/273 R; 548/336
[58] Field of Search ........................................ 424/273

[56] References Cited
U.S. PATENT DOCUMENTS 3,415,929 12/1968 Lachman et al. .................... 424/273
3,845,201 10/1974 Haddad et al. ...................... 424/273

Primary Examiner—Frederick E. Waddell
Attorney, Agent, or Firm—Charles N. Blitzer

[57] ABSTRACT

Compounds of the formula:

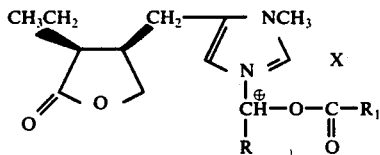

wherein R represents a member selected from the group consisting of a hydrogen atom, a $C_1$-$C_{20}$ open chain or cyclo alkyl group, a $C_1$-$C_{20}$ alkoxyalkyl group, a $C_1$-$C_{20}$ alkanoyloxyalkyl group, a $C_1$-$C_{20}$ haloalkyl group, a $C_1$-$C_{20}$ carboxyalkyl group, a phenyl group, a naphthyl group and a substituted phenyl or naphthyl group, whose substituents are selected from the group consisting of a halogen atom, an O-$C_1$-$C_4$ alkyl group, an O-$C_1$-$C_8$ alkanoyl group, a nitro group, a carboxyl group, and a carboethoxy group; wherein $R_1$ represents a $C_9$-$C_{22}$ straight or branched alkyl group, a

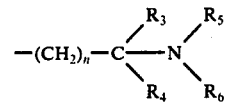

group, wherein $R_3$, $R_4$, $R_5$ and $R_6$ are each selected from the group consisting of a hydrogen atom, a methyl group, or an ethyl group, and wherein $R_1$ further represents a member selected from the group consisting of a $C_0$-$C_{22}$ straight or branched alkyl

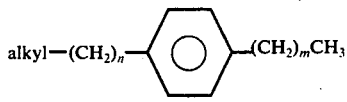

group, wherein $n$ in each occurrence and $m$ represent an integer of from 0 to 22, and an

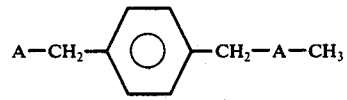

group, wherein A represents a -$(CH_2CH_2O)_p$ group, wherein the $p$ represents an integer of from 0 to 22 and a cholic acid residue; and wherein X represents a member selected from the group consisting of a halogen atom, a methanesulfonate group, a fluorosulfonate group and a tosylate group, useful in reducing intraocular pressure in warm-blooded animals are disclosed.

17 Claims, 1 Drawing Figure

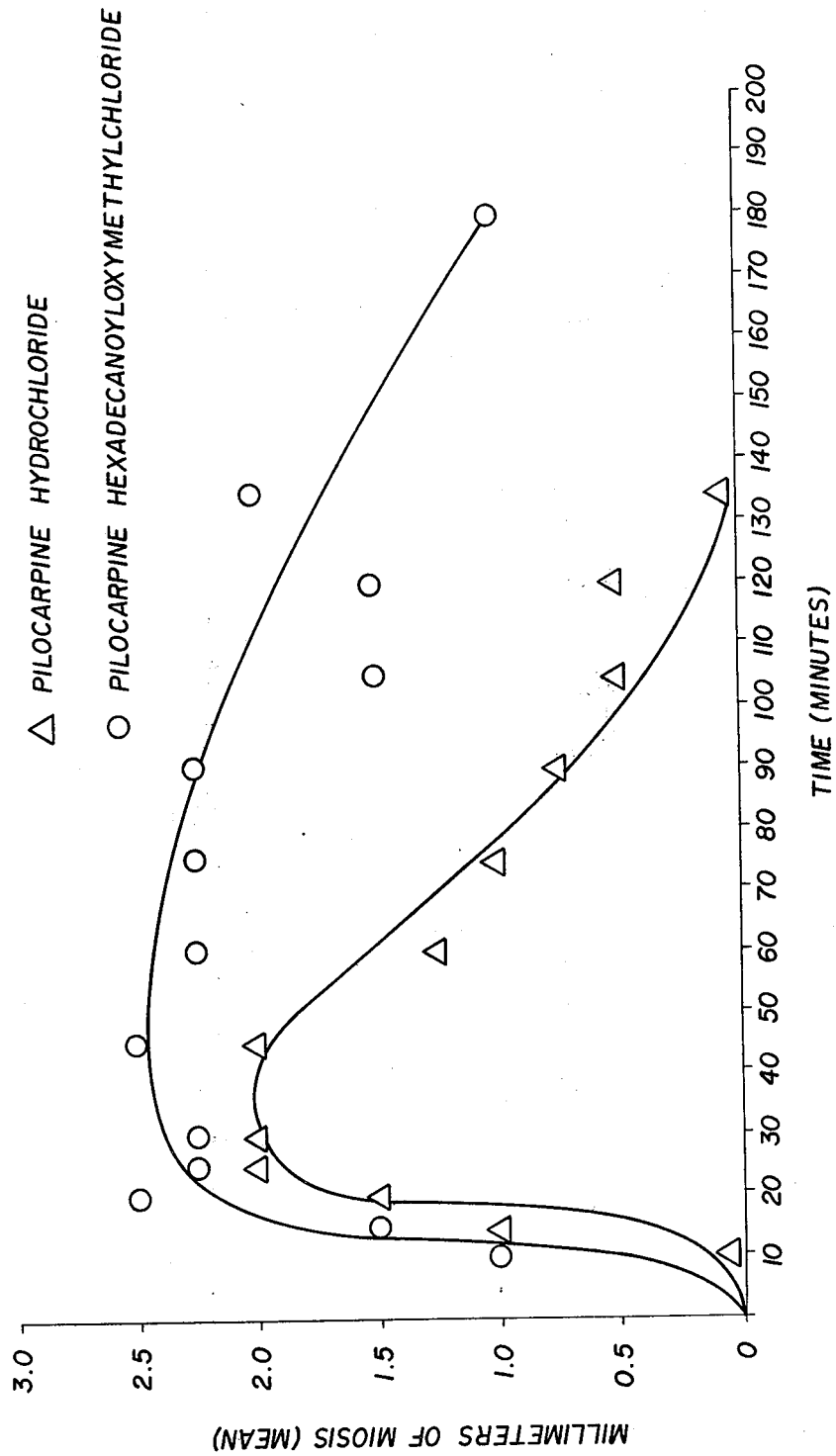

SELECTED QUATERNARY AMMONIUM SALTS OF PILOCARPINE USEFUL IN REDUCING INTRAOCULAR PRESSURE IN WARM-BLOODED ANIMALS

BACKGROUND OF THE INVENTION

1. Field of the Invention

The present invention relates to useful therapeutic quaternary ammonium salt forms of pilocarpine. More particularly, the present invention pertains to newly developed quaternary ammonium salt forms of pilocarpine which are characterized as being much more lipophilic in comparison to the parent moiety, pilocarpine, per se.

These newly developed quaternary ammonium salt forms of pilocarpine are extremely useful as antiglaucoma agents, and they can be administered topically to warm-blooded animals, e.g., humans, per se, or in any pharmaceutically acceptable ophthalmic composition form when admixed with a suitable pharmaceutically acceptable inert ophthalmic carrier.

2. Description of the Prior Art

A pharmaceutical and medical need exists for new and useful compounds indicated for the management of glaucoma in warm-blooded animals. This need exists because the compound of choice, pilocarpine, exhibits extremely poor lipoidal solubility which tends to restrict ophthalmic application of the drug in the treatment and management of glaucoma. Specifically, because of its poor lipoidal solubility, pilocarpine cannot rapidly penetrate the ophthalmic membrane, and as a consequence thereof, massive ophthalmic dosing is required in order to enable an antiglaucoma effective amount of pilocarpine to penetrate the ophthalmic membrane.

It is therefore quite obvious that a need exists for improved forms of pilocarpine which because of their extremely lipophilic nature, will rapidly penetrate the ophthalmic membrane and achieve reduction in intraocular pressure without the need for massive dosing.

SUMMARY OF THE INVENTION

Accordingly, it is an immediate object of the present invention to provide a novel series of pilocarpine derivatives which are characterized as exhibiting improved lipoidal solubility for enhanced ophthalmic absorption when administered to the ophthalmic membrane of a warm-blooded animal, e.g., human.

Another object of the present invention is to provide compounds as described above which can be administered, per se, or which can be dispensed in conventional pharmaceutically acceptable ophthalmic carriers to warm-blooded animals to produce an antiglaucoma effect.

Finally, still another object of the present invention concerns the development of compounds as described above which remain nontoxic to the warm-blooded animal so treated.

All the foregoing objects are satisfied with a compound having the formula:

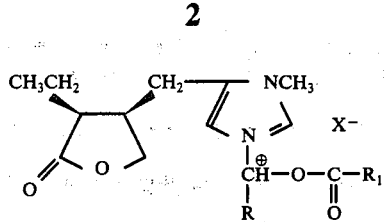

wherein R represents a member selected from the group consisting of a hydrogen atom, a $C_1-C_{20}$ open chain or cyclo alkyl group, a $C_1-C_{20}$ alkoxyalkyl group, a $C_1-C_{20}$ alkanoyloxyalkyl group, a $C_1-C_{20}$ haloalkyl group, a $C_1-C_{20}$ carboxyalkyl group, a phenyl group, a naphthyl group and a substituted phenyl or naphthyl group whose substituents are selected from the group consisting of a halogen atom, an $O-C_1-C_4$ alkyl group, an $O-C_1-C_8$ alkanoyl group, a nitro group, a carboxyl group, and a carboethoxy group; wherein $R_1$ represents a $C_9-C_{22}$ straight or branched alkyl group,

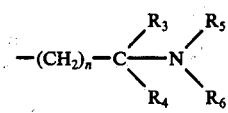

group, wherein $R_3$, $R_4$, $R_5$ and $R_6$ are each selected from the group consisting of a hydrogen atom, a methyl group, or an ethyl group, and wherein $R_1$ further represents a member selected from the group consisting of a $C_0-C_{22}$ straight or branched

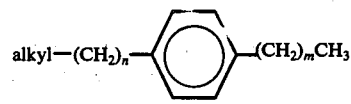

group, wherein $n$ in each occurrence and $m$ represent an integer of from 0 to 22, and an

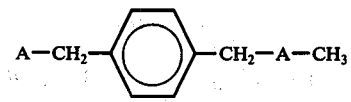

group, wherein A represents a $-(CH_2CH_2O)_p$ group, wherein the $p$ represents an integer of from 0 to 22 and a cholic acid residue; and wherein X represents a member selected from the group consisting of a halogen atom, a methanesulfonate group, a fluorosulfonate group and a tosylate group.

With regard to the above formula, reference to "halogen" in each occurrence denotes any suitable member of the halogen series, e.g., chlorine, bromine or iodine; and reference to "alkanoyl" in the expression O-alkanoyl denotes any convenient alkanoyl group such as a formyl group, an acetyl group, a propionyl group, a benzoyl group, etc. It is further noted that the term "substituted" insofar as "substituted phenyl or naphthyl" is concerned refers to the fact that the aryl function may be substituted with any one or more of those substituents specifically defined herein.

DETAILED DESCRIPTION OF THE PREFERRED EMBODIMENTS

While all the compounds encompassed within the above generic formula meet the present inventor's criteria, nevertheless, certain compounds remain preferred as set out below. Additional preferred compounds can be found in the examples which follow:

1. 1-n-Octanoyloxymethyl-pilocarpine chloride or bromide.
2. 1-n-Dodecanoyloxymethyl-pilocarpine chloride or bromide.
3. 1-n-Tetradecanoyloxymethyl-pilocarpine chloride or bromide.
4. 1-n-Hexadecanoyloxymethyl-pilocarpine chloride or bromide.
5. 1-n-Decanoyloxymethyl-pilocarpine chloride or bromide.
6. 1-[α-(n-Octanoyloxy)ethyl]-pilocarpine chloride or bromide.
7. 1-[α-(n-Decanoyloxy)ethyl]-pilocarpine chloride or bromide.
8. 1-[α-(n-Dodecanoyloxy)ethyl]-pilocarpine chloride or bromide.
9. 1-[α-(n-Hexadecanoyloxy)ethyl]-pilocarpine chloride or bromide.
10. 1-Oleyloxymethyl-pilocarpine chloride or bromide.
11. 1-[α-(n-Decanoyloxy)benzyl]-pilocarpine chloride or bromide.
12. 1-[α-(n-Dodecanoyloxy)benzyl]-pilocarpine chloride or bromide.
13. 1-[α-(n-Tetradecanoyloxy)benzyl]-pilocarpine chloride or bromide.
14. 1-[α-(n-Hexadecanoyloxy)benzyl]-pilocarpine chloride or bromide.
15. 1-(α-Oleyloxy-benzyl)-pilocarpine chloride or bromide.

The compounds of the present invention can be conveniently prepared in the manner described below:

METHOD "A"

React an α-halo-ester of the general formula:

$$\underset{R-C-O-CH-X}{\overset{O\quad\quad R_1}{\underset{\parallel\quad\quad |}{}}}$$

wherein R, $R_1$ and X are defined as above, directly with pilocarpine in approximately equimolecular proportions, in the presence of an inert solvent (ether, acetonitrile, $CH_2Cl_2$, etc.) at room temperature or at the reflux temperature of the solvent for 2 – 24 hours. As an alternative procedure, the above reaction can be carried out in the absence of a solvent by mixing the above two reactants together and maintaining them at room temperature or between 20° – 70° C for 2 – 24 hours. In both cases, the crystalline salt formed can be purified by crystallization from an ether-ethanol mixture, or the like.

METHOD "B"

The same compounds can be obtained by first mixing pilocarpine with an equimolecular amount of the corresponding acyl halide $$\underset{(R-C-X)}{\overset{O}{\underset{\parallel}{}}},$$

maintaining the mixture at room temperature for 2 – 24 hours. Then there is added to the reaction mixture an equimolecular amount of the aldehyde ($R_1$ - CHO). The mixture is then stirred at room temperature or elevated temperature, up to 75° C, for 2 – 48 hours. Purification of the final product is carried out as in Method "A".

In the above description of Method "B", R, $R_1$ and X are defined as above.

Without further elaboration, it is believed that one of ordinary skill in the art can, using the preceding description, utilize the present invention to its fullest extent. Consequently, the following preferred specific embodiments are to be construed as merely illustrative and not limitative of the remainder of the specification and claims in any way whatsoever. Reference to temperature denotes Centigrade unless otherwise indicated.

EXAMPLE I

Preparation of Some Selected Compounds of the Present Invention

A series of chloroalkyl n-alkylcarboxylates (1 a – e) were prepared by reaction of the corresponding acyl chloride with the appropriate aldehyde in the presence of a catalytic amount of anhydrous zinc chloride (SCHEME 1).[1]

REFERENCES 1. a. R. Adams and E. H. Vollweiler, J. Amer. Chem. Soc., 40, 1732 (1918). b. H. E. French and R. Adams, ibid., 43, 651 (1921). c. L. H. Ulich and R. Adams, ibid, 43, 660 (1921).

$$CH_3(CH_2)_nCOCl + (RCHO)_x \xrightarrow{ZnCl_2} CH_3(CH_2)_n CO_2\overset{R}{\underset{|}{C}}HCl$$

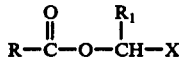

| | | |
|---|---|---|
| a | n = 10 | R = H |
| b | n = 10 | R = $CH_3$ |
| c | n = 12 | R = H |
| d | n = 14 | R = H |
| e | n = 14 | R = $CH_3$ |

A series of n-alkylcarboxyalkyl-pilocarpine quaternary salts (2 a – e) were prepared by reaction of the corresponding chloroalkyl n-alkylcarboxylates with pilocarpine (SCHEME 2).

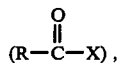

| | | |
|---|---|---|
| a | n = 10 | R = H |
| b | n = 10 | R = $CH_3$ |
| c | n = 12 | R = H |
| d | n = 14 | R = H |
| e | n = 14 | R = $CH_3$ | n-Dodecanoyloxymethyl-pilocarpine chloride (2 a):

A mixture of 2.48 g (0.01 mol) chloromethyl n-dodecanoate (1 a) and 2.08 g (0.01 mol) pilocarpine were mixed and heated together at 90° for 3 hours. On cooling to room temperature, anhydrous ether was added to the mixture and the mixture was triturated in anhydrous ether overnight. The solid was isolated by filtration under a nitrogen atmosphere and thoroughly washed with anhydrous ether. After drying in vacuo over calcium sulfate at room temperature, 3.19 g (0.007 mol), 70%, 2 a was obtained as a white, hygroscopic solid, mp 58° - 61°, pmr (CDCl$_3$) δ 10.3 (s, 1H) 7.7 (s, 1H), 6.3 (s, 2H), 4.6 - 3.6 (7H), 3.4 - 1.5 (7H), 1.3 (bs, 20H) and 0.9 (bt, 3H) ppm.

Anal. Calcd for C$_{24}$H$_{41}$ClN$_2$O$_4$: C, 63.07; H, 9.04; N, 6.13. Found: C, 63.11; H, 9.18; N, 6.34.

Following the procedure described for the preparation of 2 a the following n-alkylcarboxyalkyl-pilocarpine quaternary salts were prepared:

n-Dodecanoyl-α-oxyethyl-pilocarpine chloride (2 b):

mp 96° - 101° C; ir (KBr) 3040, 2920, 2840, 1740, 1560, 1465, 1170, 1140, 1095, 1015 and 930 cm$^{-1}$; pmr (CDCl$_3$) δ 10.6 (s, 1H), 8.0 (s, 1H), 6.9 (q, 1H), 4.7 - 3.8 (7H), 3.5 - 1.5 (10 H), 1.3 (bs, 20) and 0.9 (bt, 3H) ppm.

Anal. Calcd for C$_{25}$H$_{43}$ClN$_2$O$_4$: C, 63.74; H, 9.20. Found: C, 63.07; H, 9.03.

n-Tetradecanoyloxymethyl-pilocarpine chloride (2 c):

mp 59° - 64° C; pmr (CDCl$_3$) δ 10.4 (s, 1H), 7.8 (s, 1H), 6.3 (s, 2H), 4.5 - 3.7 (7H), 3.3 - 1.5 (7H), 1.2 (bs, 24H) and 0.9 (bt, 3H) ppm.

Anal. Calcd for C$_{26}$H$_{45}$ClN$_2$O$_4$: C, 64.37; H, 9.35; N, 5.78. Found: C, 64.14; H, 9.31; N, 5.98.

n-Hexadecanoyloxymethyl-pilocarpine chloride (2 d):

mp 67° - 72° C; ir (KBr) 3020, 2900, 2840, 1740, 1550, 1450, 1370, 1160, 1120, 1015 and 965 cm$^{-1}$; uv (CHCl$_3$) λ 239 nm, ε = 917 M$^{-1}$cm$^{-1}$; pmr (CDCl$_3$) δ 10.3 (s, 1H), 7.7 (s, 1H), 6.3 (s, 2H), 4.6 - 3.8 (7H), 3.4 - 1.5 (7H), 1.3 (bs, 28H) and 0.9 (bt, 3H) ppm.

Anal. Calcd for C$_{28}$H$_{49}$ClN$_2$O$_4$: C, 65.53; H, 9.62; N, 5.46. Found: C, 65.20; H, 9.67; N, 5.60.

n-Hexadecanoyl-α-oxyethyl-pilocarpine chloride (2 e):

mp 115° - 119° C; ir (KBr) 3040, 2920, 2840, 1745, 1560, 1470, 1175, 1140, 1100, 1015, 930 and 725 cm$^{-1}$; pmr (CDCl$_3$) δ 10.6 (s, 1H), 8.0 (s, 1H), 7.0 (q, 1H), 4.7 - 4.0 (7H), 3.6 - 1.5 (10H), 1.3 (bs, 28H) and 0.9 bt, 3H) ppm.

Anal. Calcd for C$_{29}$H$_{51}$ClN$_2$O$_4$: C, 66.07; H, 9.75; N, 5.32. Found: C, 65.31; H, 9.62; N, 5.88.

By following the preceding example and substituting the generically and/or specifically described reactants and/or operating conditions of this invention, the following additional compounds can be prepared.

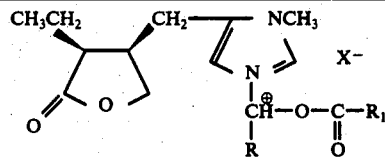

| R | R$_1$ | X$^⊖$ |
|---|---|---|
| H | CH$_3$(CH$_2$)$_9$— | Cl or Br |
| H | CH$_3$(CH$_2$)$_7$CH=CH(CH$_2$)$_7$— | Cl or Br |
| H | CH$_2$(CH$_2$)$_3$—C$_6$H$_4$—(CH$_2$)$_5$— | Cl or Br |
| H | (CH$_3$)$_3$C—CH$_2$—C(CH$_3$)$_2$—C$_6$H$_4$—O—CH$_2$—CH$_2$OCH$_2$CH$_2$O—CH$_2$— | Cl or Br |
| H | (CH$_3$)$_2$N—(CH$_2$)$_{11}$— | Cl or Br |
| H | (CH$_3$)$_2$N—C(O)—(CH$_2$)$_{11}$— | Cl or Br |
| CH$_3$ | CH$_3$(CH$_2$)$_9$— | Cl or Br |
| CH$_3$ | CH$_3$(CH$_2$)$_{11}$— | Cl or Br |
| CH$_3$ | CH$_3$(CH$_2$)$_{13}$— | Cl or Br |
| CH$_3$ | CH$_3$(CH$_2$)$_{15}$— | Cl or Br |
| CH$_3$ | CH$_3$(CH$_2$)$_7$C=CH(CH$_2$)$_7$— | Cl or Br |
| CH$_3$ | CH$_2$(CH$_2$)$_3$—C$_6$H$_4$—(CH$_2$)$_5$— | |
| CH$_3$ | (CH$_3$)$_3$C—CH$_2$—C(CH$_3$)$_2$—C$_6$H$_4$—O—CH$_2$—CH$_2$OCH$_2$CH$_2$OCH$_2$— | Cl or Br |
| CH$_3$ | (CH$_3$)$_2$N—(CH$_2$)$_{11}$— | Cl or Br |
| CCl$_3$ | (CH$_3$)$_2$N—C(O)—(CH$_2$)$_{11}$— | Cl or Br |
| CCl$_3$ | CH$_3$(CH$_2$)$_9$— | Cl or Br |
| CCl$_3$ | CH$_3$(CH$_2$)$_{11}$— | Cl or Br |
| CCl$_3$ | CH$_3$(CH$_2$)$_{13}$— | Cl or Br |
| CCl$_3$ | CH$_3$(CH$_2$)$_{15}$— | Cl or Br |
| CCl$_3$ | CH$_3$(CH$_2$)$_7$CH=CH(CH$_2$)$_7$— | Cl or Br |
| CCl$_3$ | CH$_2$(CH$_2$)$_3$—C$_6$H$_4$—(CH$_2$)$_5$— | Cl or Br |
| CCl$_3$ | (CH$_3$)$_3$C—CH$_2$—C(CH$_3$)$_2$—C$_6$H$_4$—O—CH$_2$—CH$_2$OCH$_2$CH$_2$O—CH$_2$— | Cl or Br |
| CCl$_3$ | (CH$_3$)$_2$N—(CH$_2$)$_{11}$— | Cl or Br |
| CCl$_3$ | (CH$_3$)$_2$N—C(O)—(CH$_2$)$_{11}$— | Cl or Br |
| C$_6$H$_5$ | CH$_3$(CH$_2$)$_9$— | Cl or Br |
| C$_6$H$_5$ | CH$_3$(CH$_2$)$_{11}$— | Cl or Br |
| C$_6$H$_5$ | CH$_3$(CH$_2$)$_{13}$— | Cl or Br |
| C$_6$H$_5$ | CH$_3$(CH$_2$)$_{15}$— | Cl or Br |
| C$_6$H$_5$ | CH$_3$(CH$_2$)$_7$CH=CH(CH$_2$)$_7$— | Cl or Br |
| C$_6$H$_5$ | CH$_2$(CH$_2$)$_3$—C$_6$H$_4$—(CH$_2$)$_5$— | Cl or Br |
| C$_6$H$_5$ | (CH$_3$)$_3$C—CH$_2$—C(CH$_3$)$_2$—C$_6$H$_4$—O—CH$_2$—CH$_2$OCH$_2$CH$_2$O—CH$_2$— | Cl or Br |
| C$_6$H$_5$ | (CH$_3$)$_2$N—(CH$_2$)$_{11}$— | Cl or Br |
| C$_6$H$_5$ | (CH$_3$)$_2$N—C(O)—(CH$_2$)$_{11}$— | Cl or Br |

EXAMPLE II

OPHTHALMIC MIOSIS STUDY 3-n-Hexadecanoyloxymethyl-pilocarpine chloride

An equivalent of a 2% pilocarpine solution of the hydrochloride and the hexadecanoyloxymethyl chloride salt of pilocarpine were compared for miotic activity in the eyes of albino female rabbits. The results are represented graphically in FIG. "1" accompanying this application. It is quite obvious that the quaternary salt form (hexadecanoyloxymethyl chloride) releases pilocarpine and induces pilocarpine activity, but most importantly, at a more dramatic sustained rate when compared to pilocarpine, per se.

Substantially similar miotic values are observed with the remaining compounds of the present application.

All the compounds of the present invention are conveniently administered, per se, or in combination with any pharmaceutically acceptable inert ophthalmic carrier which include, without limitation, conventional phosphate buffer vehicle systems, isotonic boric acid vehicles, isotonic sodium chloride vehicles, isotonic sodium borate vehicles, and the like. Such can be readily ascertained by simply referring to the text entitled "REMINGTON'S PHARMACEUTICAL SCIENCES," Fourteenth Edition (1970).

The dose administered, whether a single dose or a daily dose, will, of course, vary with the needs of the individual being treated. However, the dosage administered is not subject to definite bounds, but it will usually be an effective antiglaucoma amount, or the equivalent of a molar bisis of the pharmacologically active form produced upon the metabolic release of the active drug to achieve its desired pharmacological or physiological effect. Normally, the medical dose for warm-blooded animals, including humans and primates, will be in the range of about 0.01 percent to 5.0 percent, with 0.3 percent to 0.5 percent being preferred. Administration of an ophthalmic solution containing the active compound to the eye can be made via eyedrop, ophthalmic aerosol, etc.

From the foregoing description, one of ordinary skill in the art can easily ascertain the essential characteristics of the instant invention, and without departing from the spirit and scope thereof, can make various changes and modifications of the invention to adapt it to various usages and conditions. As such, these changes and/or modifications are properly, equitably and intended to be, within the full range of equivalence of the following claims.

What I claim is:

1. A method for reducing intracular pressure in a warm-blooded animal in need of said response which comprises topically administering to the ophthalmic membrane thereof, an effective amount of a compound having the formula:

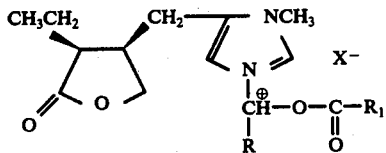

wherein R represents a member selected from the group consisting of a hydrogen atom, a $C_1$-$C_{20}$ open chain or cyclo alkyl group, a $C_1$-$C_{20}$ alkoxyalkyl group, a $C_1$-$C_{20}$ alkanoyloxyalkyl group, a $C_1$-$C_{20}$ haloalkyl group, a $C_1$-$C_{20}$ carboxyalkyl group, a phenyl group, a naphthyl group and a substituted phenyl or naphthyl group whose substituents are selected from the group consisting of a halogen atom, an O-$C_1$-$C_4$ alkyl group, an O-$C_1$-$C_8$ alkanoyl group, a nitro group, a carboxyl group, and a carboethoxy group; wherein $R_1$ represents a $C_9$-$C_{22}$ straight or branched alkyl group,

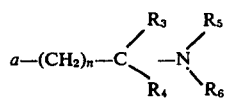

group, wherein $R_3$, $R_4$, $R_5$ and $R_6$ are each selected from the group consisting of a hydrogen atom, a methyl group, or an ethyl group, and wherein $R_1$ further represents a member selected from the group consisting of a $C_0$-$O_{22}$ straight or branched

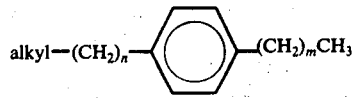

group, wherein $n$ in each occurrence and $m$ represent an integer of from 0 to 22, and an

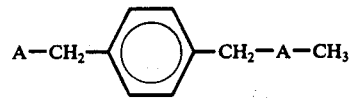

group, wherein A represents a -$(CH_2CH_2O)_p$ group, wherein the $p$ represents an integer of from 0 to 22 and a cholic acid residue; and wherein X represents a member selected from the group consisting of a halogen atom, a methanesulfonate group, a fluorosulfonate group and a tosylate group.

2. The method of claim 1, wherein said compound is: 1-n-Octanoyloxymethyl-pilocarpine chloride or bromide.

3. The method of claim 1, wherein said compound is: 1-n-Dodecanoyloxymethyl-pilocarpine chloride or bromide.

4. The method of claim 1, wherein said compound is: 1-n-Tetradecanoyloxymethyl-pilocarpine chloride or bromide.

5. The method of claim 1, wherein said compound is: 1-n-Hexadecanoyloxymethyl-pilocarpine chloride or bromide.

6. The method of claim 1, wherein said compound is: 1-n-Decanoyloxymethyl-pilocarpine chloride or bromide.

7. The method of claim 1, wherein said compound is: 1-[α-(n-Octanoyloxy)ethyl]-pilocarpine chloride or bromide.

8. The method of claim 1, wherein said compound is: 1-[α-(n-Decanoyloxy)ethyl]-pilocarpine chloride or bromide.

9. The method of claim 1, wherein said compound is: 1-[α-(n-Dodecanoyloxy)ethyl]-pilocarpine chloride or bromide.

10. The method of claim 1, wherein said compound is: 1-[α-(n-Hexadecanoyloxy)ethyl]-pilocarpine chloride or bromide.

11. The method of claim 1, wherein said compound is: 1-Oleyloxymethyl-pilocarpine chloride or bromide.

12. The method of claim 1, wherein said compound is: 1-[α-(n-Decanoyloxy)benzyl]-pilocarpine chloride or bromide.

13. The method of claim 1, wherein said compound is: 1-[α-(n-Dodecanoyloxy)benzyl]-pilocarpine chloride or bromide.

14. The method of claim 1, wherein said compound is: 1-[α-(n-tetradecanoyloxy)benzyl]-pilocarpine chloride or bromide.

15. The method of claim 1, wherein said compound is: 1-[α-(n-Hexadecanoyloxy)benzyl]-pilocarpine chloride or bromide.

16. The method of claim 1, wherein said compound is: 1-(α-Oleyloxy-benzyl)-pilocarpine chloride or bromide.

17. The method of claim 1, wherein said compound is administered in combination with a topical ophthalmic inert carrier.

* * * * *